(12) United States Patent
Darga et al.

(10) Patent No.: US 9,468,736 B2
(45) Date of Patent: *Oct. 18, 2016

(54) FUEL CELL INTERCONNECT WITH REDUCED VOLTAGE DEGRADATION OVER TIME

(71) Applicant: BLOOM ENERGY CORPORATION, Sunnyvale, CA (US)

(72) Inventors: Daniel Darga, Pleasanton, CA (US); Tad Armstrong, Burlingame, CA (US); Vijay Srivatsan, Sacramento, CA (US); Harald Herchen, Los Altos, CA (US); Cheng-Yu Lin, Sunnyvale, CA (US)

(73) Assignee: BLOOM ENERGY CORPORATION, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/543,095

(22) Filed: Nov. 17, 2014

(65) Prior Publication Data

US 2015/0147679 A1    May 28, 2015

Related U.S. Application Data

(60) Provisional application No. 61/909,426, filed on Nov. 27, 2013.

(51) Int. Cl.

| | |
|---|---|
| *H01M 8/0208* | (2016.01) |
| *H01M 8/0228* | (2016.01) |
| *A61M 16/14* | (2006.01) |
| *A61M 16/04* | (2006.01) |
| *A61M 16/06* | (2006.01) |
| *A61M 16/20* | (2006.01) |
| *A61M 15/00* | (2006.01) |
| *A61M 16/08* | (2006.01) |

(52) U.S. Cl.
CPC ......... *A61M 16/14* (2013.01); *A61M 15/0015* (2014.02); *A61M 15/0018* (2014.02); *A61M 15/0021* (2014.02); *A61M 15/0086* (2013.01); *A61M 16/04* (2013.01); *A61M 16/06* (2013.01); *A61M 16/0816* (2013.01); *A61M 16/208* (2013.01); *A61M 15/0065* (2013.01); *A61M 16/08* (2013.01); *A61M 2205/0233* (2013.01); *A61M 2240/00* (2013.01)

(58) Field of Classification Search
CPC ........... H01M 8/0208; H01M 8/0228; H01M 8/2465; H01M 2008/1294
See application file for complete search history.

(56) References Cited

U.S. PATENT DOCUMENTS

| | | |
|---|---|---|
| 4,135,041 A | 1/1979 | Jung et al. |
| 4,755,429 A | 7/1988 | Nickols et al. |
| 4,913,982 A | 4/1990 | Kotchick et al. |
| 5,162,167 A | 11/1992 | Minh et al. |
| 5,213,910 A | 5/1993 | Yamada |
| 5,215,946 A | 6/1993 | Minh |
| 5,248,712 A | 9/1993 | Takeuchi et al. |
| 5,256,499 A | 10/1993 | Minh et al. |
| 5,273,837 A | 12/1993 | Aitken et al. |
| 5,290,642 A | 3/1994 | Minh et al. |
| 5,342,705 A | 8/1994 | Minh et al. |
| 5,368,667 A | 11/1994 | Minh et al. |
| 5,382,315 A | 1/1995 | Kumar |
| 5,385,792 A | 1/1995 | Shiratori et al. |
| 5,453,331 A | 9/1995 | Bloom et al. |
| 5,494,700 A | 2/1996 | Anderson et al. |
| 5,501,914 A | 3/1996 | Satake et al. |
| 5,518,829 A | 5/1996 | Satake et al. |
| 5,589,017 A | 12/1996 | Minh |
| 5,641,585 A | 6/1997 | Lessing et al. |
| 5,733,499 A | 3/1998 | Takeuchi et al. |
| 5,942,349 A | 8/1999 | Badwal et al. |
| 5,955,392 A | 9/1999 | Takeuchi et al. |
| 6,001,761 A | 12/1999 | Hata et al. |
| 6,361,892 B1 | 3/2002 | Ruhl et al. |
| 6,492,053 B1 | 12/2002 | Donelson et al. |
| 6,582,845 B2 | 6/2003 | Helfinstine et al. |
| 6,589,681 B1 | 7/2003 | Yamanis |
| 6,638,575 B1 | 10/2003 | Chen et al. |
| 6,835,488 B2 | 12/2004 | Sasahara et al. |
| 7,045,237 B2 | 5/2006 | Sridhar et al. |
| 8,241,817 B2 | 8/2012 | Yang et al. |

(Continued)

FOREIGN PATENT DOCUMENTS

| | | |
|---|---|---|
| EP | 0615299 A1 | 9/1994 |
| JP | 06-215778 | 8/1994 |

(Continued)

OTHER PUBLICATIONS

International Search Report & Written Opinionreceived in connection with International Application No. PCT/US2014/065877, mailed Feb. 26, 2015.

(Continued)

*Primary Examiner* — Ula C Ruddock
*Assistant Examiner* — Thomas Parsons
(74) *Attorney, Agent, or Firm* — The Marbury Law Group PLLC

(57) ABSTRACT

A method of making an interconnect for a solid oxide fuel cell stack includes providing a chromium alloy interconnect and providing a nickel mesh in contact with a fuel side of the interconnect. Formation of a chromium oxide layer is reduced or avoided in locations between the nickel mesh and the fuel side of the interconnect. A Cr—Ni alloy or a Cr—Fe—Ni alloy is located at least in the fuel side of the interconnect under the nickel mesh.

22 Claims, 11 Drawing Sheets

(56) References Cited

U.S. PATENT DOCUMENTS

| | | | |
|---|---|---|---|
| 2002/0012825 | A1 | 1/2002 | Sasahara et al. |
| 2002/0132156 | A1 | 9/2002 | Ruhl et al. |
| 2003/0170527 | A1 | 9/2003 | Finn et al. |
| 2003/0180602 | A1 | 9/2003 | Finn |
| 2004/0101742 | A1 | 5/2004 | Simpkins et al. |
| 2004/0200187 | A1 | 10/2004 | Warrier et al. |
| 2005/0017055 | A1 | 1/2005 | Kurz et al. |
| 2005/0136312 | A1 | 6/2005 | Bourgeois et al. |
| 2005/0227134 | A1 | 10/2005 | Nguyen |
| 2005/0255355 | A1 | 11/2005 | Ukai et al. |
| 2006/0193971 | A1 | 8/2006 | Tietz et al. |
| 2007/0134532 | A1 | 6/2007 | Jacobson et al. |
| 2007/0231676 | A1 | 10/2007 | Cassidy et al. |
| 2008/0081223 | A1 | 4/2008 | Yasumoto et al. |
| 2008/0193825 | A1 | 8/2008 | Nguyen et al. |
| 2009/0068055 | A1 | 3/2009 | Sreedhara et al. |
| 2009/0075125 | A1* | 3/2009 | Gottmann .......... H01M 4/8657 429/529 |
| 2009/0253020 | A1 | 10/2009 | Niewolak et al. |
| 2010/0015473 | A1 | 1/2010 | Hendriksen et al. |
| 2010/0055533 | A1 | 3/2010 | Kebbede et al. |
| 2010/0119917 | A1 | 5/2010 | Kumar et al. |
| 2010/0159344 | A1 | 6/2010 | Gottmann et al. |
| 2010/0178589 | A1 | 7/2010 | Kwon et al. |
| 2011/0039183 | A1 | 2/2011 | Armstrong et al. |
| 2012/0028162 | A1 | 2/2012 | Gottmann et al. |
| 2012/0295183 | A1 | 11/2012 | Yamanis et al. |
| 2013/0230644 | A1 | 9/2013 | Armstrong et al. |
| 2015/0311538 | A1* | 10/2015 | Batawi ............... H01M 8/0208 429/454 |

FOREIGN PATENT DOCUMENTS

| | | |
|---|---|---|
| JP | 09-199143 | 7/1997 |
| JP | 09-223506 | 8/1997 |
| JP | 09-245810 | 9/1997 |
| JP | 09-245811 | 9/1997 |
| JP | 09-277226 | 10/1997 |
| JP | 2000-281438 | 10/2000 |
| JP | 2009-212046 | 9/2009 |
| WO | WO2006/016628 A1 | 2/2006 |
| WO | WO 2011/096939 A1 | 8/2011 |
| WO | WO 2013/130515 A1 | 2/2013 |

OTHER PUBLICATIONS

Haynes International High-Temperature Alloys, "HAYNES (Reg.) 214 (TM) alloy", 1996, pp. 1-19.
Haynes International High-Temperature Alloys, "HAYNES (Reg.) 230(TM) alloy", 2004, pp. 1-27.
International Search Report & Written Opinion, International Application No. PCT/US2007/08224, Nov. 26, 2008, 10 pgs.
International Search Report, International Application No. PCT/US2003/04808, Aug. 19, 2003, 9pgs.
Supplementary European Search Report, International Application No. PCT/US2003/04808, Jun. 2, 2008, 3pgs.
International Search Report & Written Opinion, International Application No. PCT/US2010/027899, Oct. 20, 2010, 11pgs.
International Preliminary Report on Patentability, International Application No. PCT/US2010/027899, Sep. 20, 2011, 6pgs.
International Preliminary Report on Patentability received in connection with International Application No. PCT/US2012/065213; dated May 30, 2014.
Stevenson, J.W. et al., "SECA Core Technology Program: Materials Development at PNNL," Pacific Northwest National Laboratory, Richland, WA, SECA Core Technology Review Meeting, Lakewood, CO, Oct. 25, 2005.
International Search Report and Written Opinion received in connection with international application No. PCT/US2013/027895; dated Jun. 24, 2013.
International Preliminary Report on Patentability received in connection with international application No. PCT/US2013/027895; dated Sep. 12, 2014.
Batawi, E. et al., "Multi-Layered Coating Providing Corrosion Resistance to Zirconia Based Electrolytes," U.S. Appl. No. 13/677,836, filed Nov. 15, 2012.
Wilson, J. et al., "Coatings for Metal Interconnects to Reduce SOFC Degradation," U.S. Appl. No. 13/409,629, filed Mar. 1, 2012.
Armstrong, T. et al., "Coatings for SOFC Metallic Interconnects," US Appl. No. 13/781,206, filed Feb. 28, 2013.
La O, G. J. et al., "Investigation of Oxygen Reduction Mechanisms Using Cathode Microelectrodes Part I: Experimental Analysis of La Sr MnO and Platinum," $207^{th}$ Meeting of the Electornchemical Society, Quebec City, May 15-20 2005, Submitted to Symposium Q1—Ninth International Symposium on SOFCs (SOFC IX) 2005.

* cited by examiner

FUEL CELL INTERCONNECT WITH REDUCED VOLTAGE DEGRADATION OVER TIME

FIELD

The present invention is directed to fuel cell stack components, specifically to interconnects and methods of making interconnects for fuel cell stacks.

BACKGROUND

A typical solid oxide fuel cell stack includes multiple fuel cells separated by metallic interconnects (IC) which provide both electrical connection between adjacent cells in the stack and channels for delivery and removal of fuel and oxidant. The metallic interconnects are commonly composed of a Cr based alloy such as an alloy known as CrF which has a composition of 95 wt % Cr-5 wt % Fe or Cr—Fe—Y having a 94 wt % Cr-5 wt % Fe-1 wt % Y composition. The CrF and CrFeY alloys retain their strength and are dimensionally stable at typical solid oxide fuel cell (SOFC) operating conditions, e.g. 700-900 C in both air and wet fuel atmospheres. However, during operation of the SOFCs, chromium in the CrF or CrFeY alloys react with oxygen and form chromia, resulting in degradation of the SOFC stack.

Two of the major degradation mechanisms affecting SOFC stacks are directly linked to chromia formation of the metallic interconnect component: i) higher stack ohmic resistance due to the formation of native chromium oxide (chromia, $Cr_2O_3$) on the interconnect, and ii) chromium poisoning of the SOFC cathode.

Although $Cr_2O_3$ is an electronic conductor, the conductivity of this material at SOFC operating temperatures (700-900 C) is very low, with values on the order of 0.01 S/cm at 850 C (versus $7.9 \times 10^4$ $Scm^{-1}$ for Cr metal). The chromium oxide layer grows in thickness on the surfaces of the interconnect with time and thus the ohmic resistance of the interconnect and therefore of the SOFC stack due to this oxide layer increases with time.

The second degradation mechanism related to the chromia forming metallic interconnects is known as chromium poisoning of the cathode. At SOFC operating temperatures, chromium vapor diffuses through cracks or pores in the coating and chromium ions can diffuse through the lattice of the interconnect coating material into the SOFC cathode via solid state diffusion. Additionally, during fuel cell operation, ambient air (humid air) flows over the air (cathode) side of the interconnect and wet fuel flows over the fuel (anode) side of the interconnect. At SOFC operating temperatures and in the presence of humid air (cathode side), chromium on the surface of the $Cr_2O_3$ layer on the interconnect reacts with water and evaporates in the form of the gaseous species chromium oxide hydroxide, $CrO_2(OH)_2$. The chromium oxide hydroxide species transports in vapor form from the interconnect surface to the cathode electrode of the fuel cell where it may deposit in the solid form, $Cr_2O_3$. The $Cr_2O_3$ deposits on and in (e.g., via grain boundary diffusion) the SOFC cathodes and/or reacts with the cathode (e.g. to form a Cr—Mn spinel), resulting in significant performance degradation of the cathode electrode. Typical SOFC cathode materials, such as perovskite materials, (e.g., LSM, LSC, LSCF, and LSF) are particularly vulnerable to chromium oxide degradation.

SUMMARY

An embodiment relates to a method of making an interconnect for a solid oxide fuel cell stack which includes providing a chromium alloy interconnect and providing a nickel mesh in contact with a fuel side of the interconnect. Formation of a chromium oxide layer is reduced or avoided in locations between the nickel mesh and the fuel side of the interconnect. A Cr—Ni alloy or a Cr—Fe—Ni alloy is located at least in the fuel side of the interconnect under the nickel mesh.

DETAILED DESCRIPTION

To limit the diffusion of chromium ions (e.g., $Cr^{3+}$) through the interconnect coating material to the SOFC cathode, materials may be selected that have few cation vacancies and thus low chromium diffusivity. A series of materials that have low cation diffusivity are in the perovskite family, such as lanthanum strontium oxide, e.g. $La_{1-x}Sr_xMnO_3$ (LSM), where $0.1 \leq x \leq 0.3$, such as $0.1 \leq x \leq 0.2$. These materials have been used as interconnect coating materials. In the case of LSM, the material has high electronic conductivity yet low anion and cation diffusion.

A second role of the interconnect coating is to suppress the formation of the native oxide on the interconnect surface. The native oxide is formed when oxygen reacts with chromium in the interconnect alloy to form a relatively high resistance layer of $Cr_2O_3$. If the interconnect coating can suppress the transport of oxygen and water vapor from the air to the surface of the interconnect, then the kinetics of oxide growth can be reduced.

Similar to chromium, oxygen (e.g., $O^{2-}$ ions) can transport through the coating via solid state diffusion or by gas transport through pores and cracks in the coating. This mechanism is also available for airborne water vapor, an accelerant for Cr evaporation and possibly oxide growth. As discussed above, in a humid air environment, chromium evaporates from the surface of $Cr_2O_3$ in the form of the gas molecule $CrO_2(OH)_2$ that can subsequently diffuse through defects, such as pore and cracks, in the coating(s). In the case of oxygen and water vapor, the molecules diffuse through the defects by either bulk diffusion or by a Knudsen diffusion process, depending on the size of the defect or pore.

Figure 1:
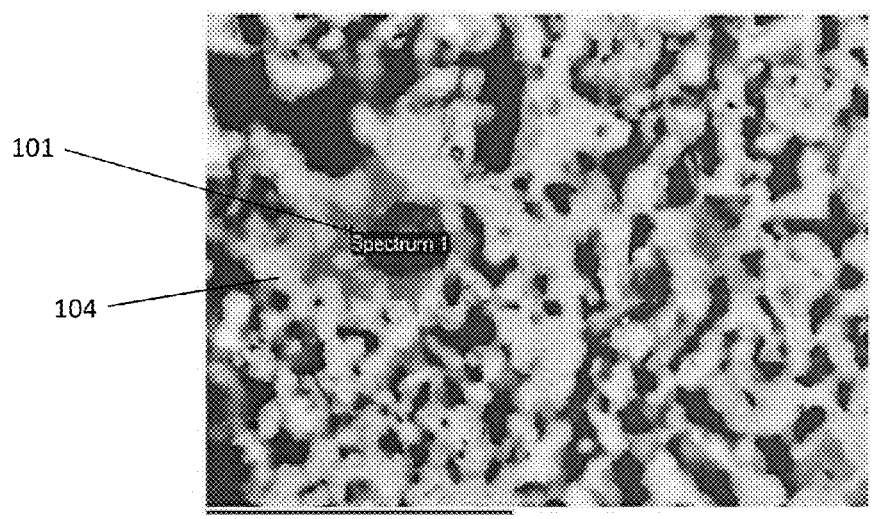
FIG. 1 is a micrograph showing a Mn—Cr spinel phase inside the pores of an LSM based cathode.
Figure 2:
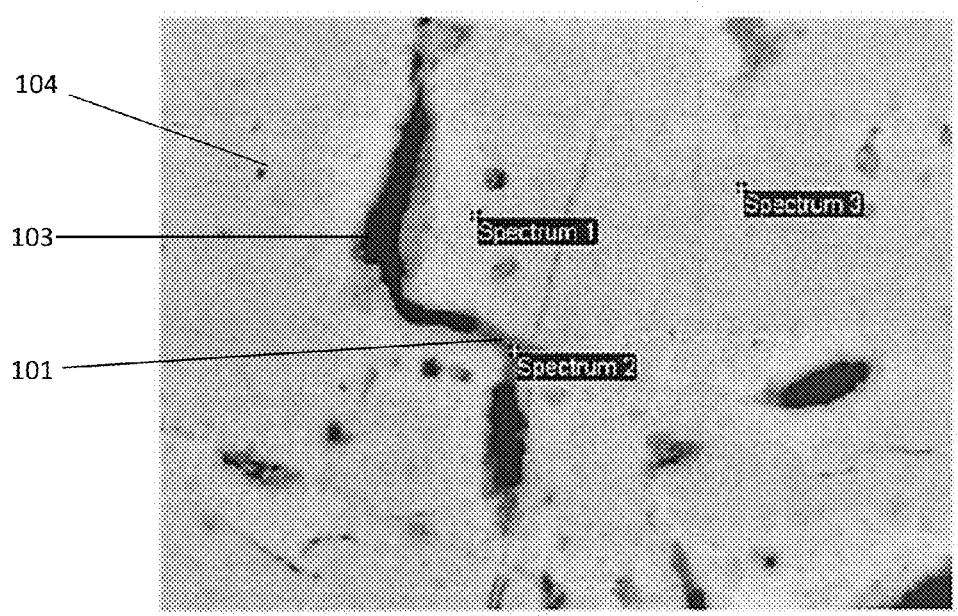
FIG. 2 is a micrograph showing a Cr containing phase in the cracks of an LSM interconnect coating that was deposited by air plasma spray. The SOFC stack was operated for 2000 hrs at 850 C.

If a $CrO_2(OH)_2$ molecule touches the coating surface, it may react to form a crystal and then re-evaporates to continue diffusing in the gas stream (in the crack or pore). Experiments have shown that $CrO_2(OH)_2$ reacts with the LSM interconnect coating 104 to form a spinel phase 101, e.g. manganese chromium oxide $(Mn, Cr)_3O_4$ as shown in FIG. 1. Although $CrO_2(OH)_2$ reacts with LSM to form the spinel phase, the chromium species is not prohibited from re-evaporating and diffusing farther down the crack or defect. Chromium has been observed transporting along the lengths of cracks in LSM IC coatings that have operated in fuel cells for extended periods of time. FIG. 2 shows chromium crystals 101 in cracks 103 in an LSM IC coating 104 that was operated in an SOFC stack for 2000 hrs under normal conditions of 800-850 C with ambient air on the cathode side. The chromium-containing crystal formations are characteristic of those formed from a vapor-to-solid phase transformation. SEM and EDS analysis of the bulk LSM coating away from the cracks do not show the presence of chromium. Therefore, it may be concluded that the majority of chromium transport from the CrF interconnect is through the LSM IC coating is via gas phase transport through and along micro- and macro-cracks, inter-particle spaces, and porosity in the LSM coating.

In the case of solid state transport, materials are chosen that have few oxide ion vacancies and thus low oxide ion conductivity. For example, the perovskite LSM is unique in that it exhibits both low cation and anion conductivity yet possesses high electronic conductivity, making it a very good coating material. Other perovskites such as $La_{1-x}Sr_xFeO_{3-d}$, $La_{1-x}Sr_xCoO_{3-d}$, and $La_{1-x}Sr_xCo_{1-y}Fe_yO_{3-d}$ all exhibit high electronic conduction and low cation conduction (low chromium diffusion rates). However, these particular materials also exhibit high oxide ion conductivities and thus are less effective at protecting the interconnect from oxidation (oxide growth).

A second material family that can be used for interconnect coating are the manganese cobalt oxide (MCO) spinel materials. In an embodiment, the MCO spinel encompasses the compositional range from $Mn_2CoO_4$ to $Co_2MnO_4$. That is, any spinel having the composition $Mn_{2-x}Co_{1+x}O_4$ ($0 \leq x \leq 1$) or written as $z(Mn_3O_4)+(1-z)(Co_3O_4)$, where ($\frac{1}{3} \leq z \leq \frac{2}{3}$) or written as $(Mn, Co)_3O_4$ may be used, such as $Mn_{1.5}Co_{1.5}O_4$, $MnCo_2O_4$ or $Mn_2CoO_4$. Many of the spinels that contain transition metals exhibit good electronic conductivities and reasonably low anion and cation diffusivities and are therefore suitable coating materials.

In an embodiment, the spinel, e.g. $(Mn, Co)_3O_4$, powder is doped with Cu to reduce the melting temperature of the spinel. The lowered melting temperature improves (increases) the coating density upon deposition with a coating method, such as air plasma spray (APS) and increases the conductivity of reaction zone oxide. The improvement in the density of the coating due to the lower melting temperature can occur during APS deposition and during operation at SOFC temperature for extended periods of time.

The addition of Cu to the spinel layer has an additional advantage. The Cu doping of the spinel, such as $(Mn, Co)_3O_4$, may result in higher electrical conductivity of the base spinel phase as well as any reaction zone oxides that form between the spinel and the native $Cr_2O_3$ oxide. Examples of electrical conductivities of oxides from the (Mn, Co, Cu, Cr)$_3O_4$ family include: $CuCr_2O_4$: 0.4 S/cm at 800 C, $Cu_{1.3}Mn_{1.7}O_4$: 225 S/cm at 750 C, and $CuMn_2O_4$: 40 S/cm at 800 C.

The spinel family of materials has the general formula $AB_2O_4$. These materials may form an octahedral or cubic crystal structure depending on the elements occupying the A and B sites. Further, depending on the doping conditions, the copper atoms may occupy either the A site, the B site or a combination of the A and B sites. Generally, Cu prefers to go into B site. When the A element is Mn, the B element is Co, and the spinel is doped with Cu, the spinel family may be described with the general formula $(Mn, Co, Cu)_3O_4$. More specifically, the spinel family may be described with the following formulas depending on location of the Cu alloying element:

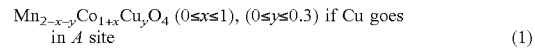

$$Mn_{2-x-y}Co_{1+x}Cu_yO_4 \ (0 \leq x \leq 1), \ (0 \leq y \leq 0.3) \text{ if Cu goes in } A \text{ site} \quad (1)$$

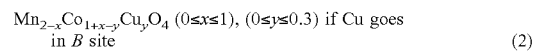

$$Mn_{2-x}Co_{1+x-y}Cu_yO_4 \ (0 \leq x \leq 1), \ (0 \leq y \leq 0.3) \text{ if Cu goes in } B \text{ site} \quad (2)$$

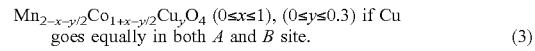

$$Mn_{2-x-y/2}Co_{1+x-y/2}Cu_yO_4 \ (0 \leq x \leq 1), \ (0 \leq y \leq 0.3) \text{ if Cu goes equally in both } A \text{ and } B \text{ site.} \quad (3)$$

Specific $(Mn, Co, Cu)_3O_4$ compositions include, but are not limited to, $Mn_{1.5}Co_{1.2}Cu_{0.3}O_4$, $Mn_{1.5}Co_{1.4}Cu_{0.1}O_4$; $Mn_2Co_{0.8}Cu_{0.2}O_4$ and $Co_2Mn_{0.8}Cu_{0.2}O_4$. Additional compositions include $Mn_2Co_{1-y}Cu_yO_4$, where ($0 \leq y \leq 0.3$), if Cu goes in B site. These composition may also be written, $(Mn_2O_3)+(1-z)(CoO)+z(CuO)$, where ($0 \leq z \leq 0.3$). Other compositions include $Co_2Mn_{1-y}Cu_yO_4$ where ($0 \leq y \leq 0.3$) if Cu goes in B site. These composition may also be written, $(Co_2O_3)+(1-z)(MnO)+z(CuO)$ where ($0 \leq z \leq 0.3$). In one preferred Mn, Co spinel composition, the Mn/Co ratio is 1.5/1.5, e.g. $Mn_{1.5}Co_{1.5}O_4$. When B site doped with Cu, preferred compositions include $Mn_{1.5}Co_{5-y}Cu_yO_4$, where ($0 \leq y \leq 0.3$).

In another embodiment, $(Mn, Co)_3O_4$ or $(Mn, Co, Cu)_3O_4$ spinel families are doped with one or more single valence species. That is, one or more species that only have one valence state. Doping with single valence species reduces cation transport at high temperature and thus reduces the thickness of the intermediate oxide layer 106. The primary ionic transport mechanism in spinels is through cation diffusion via cation vacancies in the lattice structure. In spinels with multivalent species $M^{2+/3+}$, such as $Mn^{3+/4+}$ and $Co^{2+/3+}$, cation vacancies are generated when M species are oxidized from lower to higher valence states to maintain local charge neutrality. The introduction of a single valence species typically decreases the amount of cation vacancies and decreases the amount of interdiffusion between the spinel coating 102 and the native $Cr_2O_3$ oxide or the CrF substrate 100. In this manner, the amount of the intermediate oxide layer 106 that forms is decreased. Examples of single valence species that may be introduced into the spinel coating include $Y^{3+}$, $Al^{3+}$, $Mg^{2+}$ and/or $Zn^{2+}$ metals. In an aspect, the spinel coating has a composition of $(Mn, Co, M)_3O_4$, where M=Y, Al, Mg, or Zn. For example, if M=Al doped in the A position, then the spinel compositions may include $Mn_{2-y}Al_yCoO_4$ ($0 \leq y \leq 0.3$) or $(1-z)(Mn_2O_3)+z(Al_2O_3)+CoO$, where ($0 \leq z \leq 0.15$).

In an embodiment, the interconnect coating is deposited on the Cr based alloy interconnect, such as an IC containing 93-97 wt % Cr and 3-7 wt % Fe, such as the above described Cr—Fe—Y or CrF interconnects with an air plasma spray (APS) process. The air plasma spray process is a thermal spray process in which powdered coating materials are fed into the coating apparatus. The coating particles are introduced into a plasma jet in which they are melted and then accelerated toward the substrate. On reaching the substrate, the molten droplets flatten and cool, forming the coating. The plasma may be generated by either direct current (DC plasma) or by induction (RF plasma). Further, unlike controlled atmosphere plasma spraying (CAPS) which requires an inert gas or vacuum, air plasma spraying is performed in ambient air.

Cracks in the coatings can arise at two distinct times, a) during deposition, and b) during operation in SOFC conditions. Cracks formed during deposition are influenced by both the spray gun parameters and the material's properties of the coating material. The cracks that form during operation are largely a function of the material's properties and more specially the density and sinterability of the material. Without being bound by a particular theory, it is believed that the cracking that occurs during operation is the result of continuing sintering of the coating and therefore increased densification of the coating with time. As the coatings densify, they shrink laterally. However, the coatings are constrained by the substrate and thus cracks form to relieve stress. A coating that is applied with a lower density is more likely to densify further during operation, leading to crack formation. In contrast, a coating that is applied with a higher density, is less likely to form cracks.

In a first embodiment, a sintering aid is added to the IC coating to reduce crack formation and thus decrease chromium evaporation. The sintering aid is a material which increases the as-deposited coating density and/or decreases the densification after coating deposition. Since the sintering aid increases the as-deposited density of the coating materials, it thereby reduces crack formation that occurs after the coating formation due to subsequent densification and/or operating stress on a relatively porous material. Suitable sintering aids include materials that either a) lower the melting temperature of the bulk phase of the coating materials, b) melt at a lower temperature than the bulk phase resulting in liquid phase sintering, or c) form secondary phases with lower melting temperatures. For the perovskite family, including LSM, sintering aids include Fe, Co, Ni, and Cu. These transition metals are soluble in LSM and readily dope the B-site in the $ABO_3$ perovskite phase. The melting temperature of oxides in the 3d transition metals tend to decrease in the order Fe>Co>Ni>Cu. The addition of these elements to the B-site of LSM will lower the melting temperature and improve the as-sprayed density. In an embodiment, one or more of Fe, Co, Ni and Cu are added to the coating such that the coating comprises 0.5 wt % to 5 wt %, such as 1% to 4%, such as 2% to 3% of these metals. In an alternative embodiment, the coating composition is expressed in atomic percent and comprises $La_{1-x}Sr_xMn_{1-y}M_yO_{3-d}$ where (M=Fe, Co, Ni, and/or Cu), $0.1 \leq x \leq 0.3$, $0.005 \leq y \leq 0.05$ and $0 \leq d \leq 0.3$. It should be noted that the atomic percent ranges of the Fe, Co, Ni and Cu do not necessarily have to match the weigh percent ranges of these elements from the prior embodiment.

Other elements can also be added in combination with the above transition metals to maximize conductivity, stability, and sinterability. These elements include, but are not limited to, Ba, Bi, B, Cu or any combination thereof (e.g. Cu+Ba combination), such as in a range of 5 wt % or less, such as 0.5-5 wt %. Additionally, sintering aids that specifically dope the A-site of LSM, such as Y, may be added for similar effect. An example according to this embodiment is $La_yY_xSr_{1-x-y}MnO_3$, where x=0.05-0.5, y=0.2-0.5, such as $La_{0.4}Y_{0.1}Sr_{0.5}MnO_3$. For coating materials other than LSM, copper may be used as the sintering aid in the above described MCO spinel material.

In another embodiment, rather than introducing a transition metal powder into the air plasma spray during deposition, a metal oxide powder that is easily reduced in the APS atmosphere to its metal state is added to the plasma. Preferably, the metal of the metal oxide exhibits a melting temperature lower than that of the coating phase (perovskite or spinel phase). For example, the binary oxides cobalt oxide (e.g., CoO, $Co_3O_4$, or $Co_2O_3$), NiO, $In_2O_3$, SnO, $B_2O_3$, copper oxide (e.g., CuO or $Cu_2O$), BaO, $Bi_2O_3$, ZnO or any combination thereof (e.g., (Cu,Ba)O) may be added as a second phase to the coating powder (i.e. LSM powder or La+Sr+Mn powders or their oxides). This addition, results in a two-phase powder mixture that is fed to the gun. The amount of second phase could be less than or equal to 5 wt %, such as in the range from 0.1 wt % to 5 wt % of the total powder weight.

In the APS gun, the metal oxide is reduced to its metal phase, melts, and promotes sintering of the melted LSM particles as the LSM particles solidify on the surface of the IC. The lower melting temperature of the metals and binary oxides promotes densification during deposition and solidification.

In another embodiment, a material that reacts with the coating material (such as LSM) and forms a secondary phase with a lower melting temperature is added to the coating feed during the APS process. The lower melting temperature secondary phase promotes densification. For example, silicate and/or calcium aluminate powders may react with the coating material powder(s) in the hot plasma portion of the APS gun to form glassy phases. In an embodiment, La from the LSM material reacts with a Si—Ca—Al oxide (which may also include K or Na) to form a glassy phase such as La—Ca—Si—Al oxide that forms between LSM particles. The coating may include less than or equal to 5 wt %, such as 0.5-5% of silicate, Ca—Al oxide or Si—Ca Al oxide.

In a second embodiment, the coating is post-treated in such a manner as to cause stress-free densification. This post-treatment may be performed in combination with or without the addition of the sintering aids of the first embodiment. In an example post-treatment according to the second embodiment, "redox" cycling in $N_2$ and $O_2$ atmospheres is performed. In this cycling, the coating is alternatively exposed to neutral and oxidizing atmospheres. For example, the coating may be treated in a neutral atmosphere comprising nitrogen or a noble gas (e.g., argon) and then treated in an oxidizing atmosphere comprising oxygen, water vapor, air, etc. One or more cycles may be performed, such 2, 3, 4, or more as desired. If desired, a reducing (e.g., hydrogen) atmosphere may be used instead of or in addition to the neutral atmosphere. Redox cycling in $N_2$ and $O_2$ atmospheres may cause cation vacancy concentration gradients that increase the diffusion of cation vacancies and thereby effectively increase sintering rates. This effect can be further increased by using a lower Sr content LSM coating of $La_{1-x}Sr_xMnO_{3-d}$ where x>=0.1, e.g., $0.01 \leq x \leq 0.1$, $d \leq 0.3$, such that the oxygen non-stoichiometry is maximized Use of this sintering procedure may enhance any or all of the sintering aid techniques described above.

In a third embodiment, the surface area for electrical interaction between the coating and the underlying Cr—Fe IC surface is enlarged. The chromia layer that forms between the coating and the IC causes millivolt drops over time as the chromia layer grows in thickness. The total voltage drop is dependent on the area and thickness over which the voltage drop occurs. Increasing the area of the oxide growth between the IC and the coating lowers the impact on voltage losses, thereby increasing the life of the stack. By adding what would be depth penetrations of the oxide, this embodiment effectively increases the surface area of contact and thereby reduces the impact of the growing chromia layer.

A method according to this third embodiment includes embedding small quantities of coating materials into the IC. There are two alternatives aspects of this embodiment. One aspect includes fully and uniformly distributing the coating material, such as LSM or MCO, within the IC powder (e.g., Cr—Fe powder) before compacting to form the IC. The coating powder (e.g., LSM and/or MCO powder) could be included when mixing the lubricant and Fe, Cr (or Cr—Fe alloy) powders together before compaction. Preferably, the powder mixture is able to withstand sintering temperatures and a reducing environment. The second aspect includes incorporating (e.g., embedding) a predetermined amount of coating powder only in the top surface of the Cr alloy IC. The oxide regions embedded in the surface of the CrF or CrFeY IC increase the surface roughness of the IC after the IC sintering step. The full coating is deposited on the Cr alloy interconnect after the pressing and sintering steps.

Figure 3A:
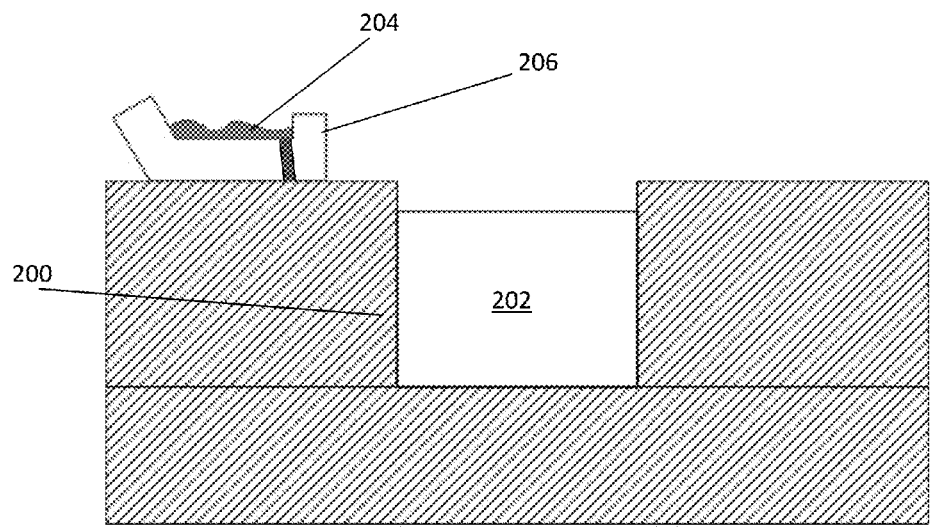
FIGS. 3A-3C are a schematic illustration of steps in a method of making an interconnect according an embodiment.
Figure 3B:
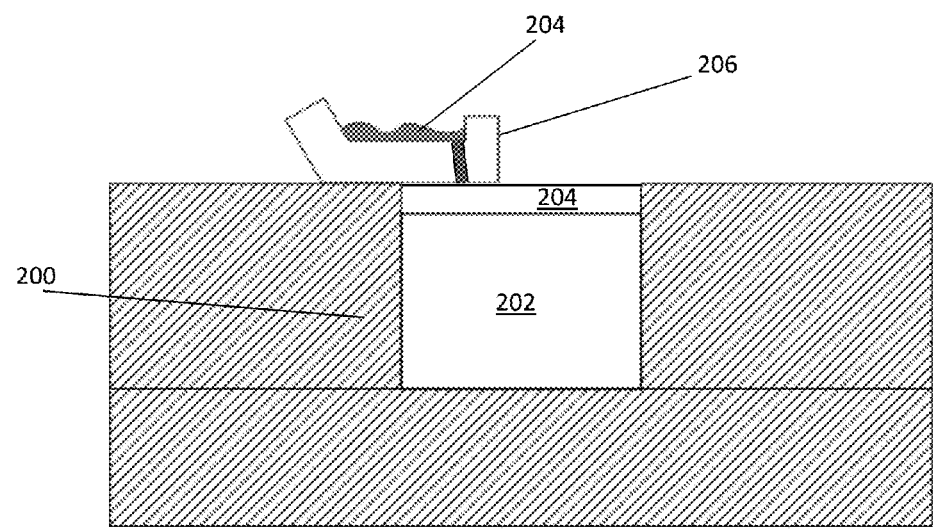
Figure 3C:
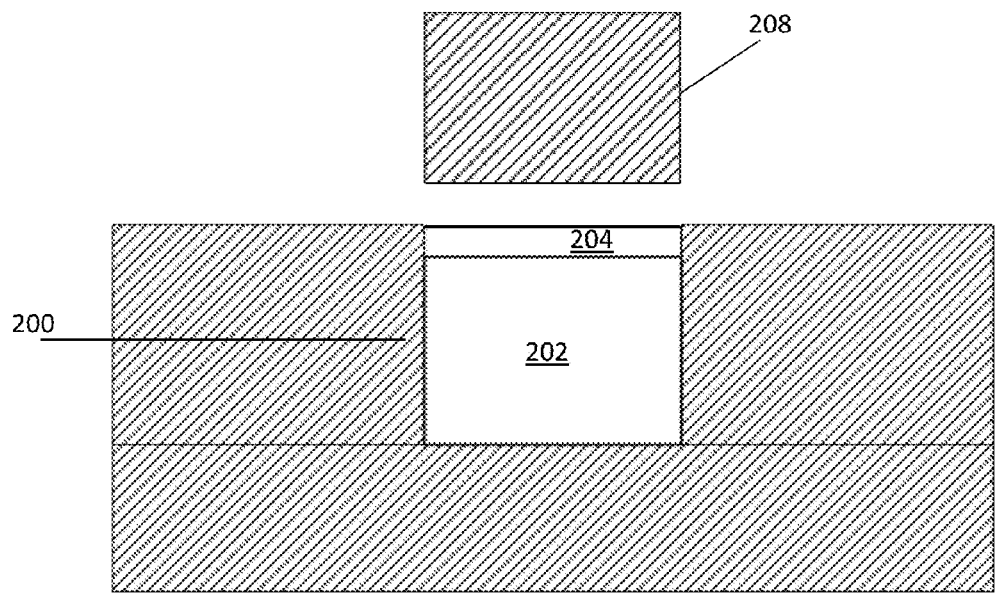

A method for embedding the coating material in the top surface of the interconnect is illustrated in FIGS. 3A-3C. The lubricant and Cr/Fe powder 202 which is used to form the bulk of the IC are added to the mold cavity 200 with a first shoe (not shown) or by another suitable method, as shown in FIG. 3A. The coating material powder 204 (e.g., LSM or MCO) or a mix of the coating material power 204 and lubricant/Cr/Fe powder 202 is provided into the mold cavity using a second shoe 206 over the powder 202 located in the mold cavity before the compaction step, as shown in FIG. 3B. The powders 204, 202 are then compacted using a punch 208, as shown in FIG. 3C, to form the interconnect having the coating material embedded in its surface on the air side (i.e., if the air side of the IC is formed facing up in the mold).

Alternatively, the coating material powder 204 (e.g., LSM or MCO) (or a mix of the coating material power 204 and lubricant/Cr/Fe powder 202) is provided into the mold cavity 200 first. The lubricant/Cr/Fe powder 202 is then provided into the mold cavity 200 over powder 204 before the compaction step if the air side of the IC is formed in the mold facing down. In this manner, the coating material is incorporated into the IC primarily at the top of the air side surface of the IC.

Figure 4:
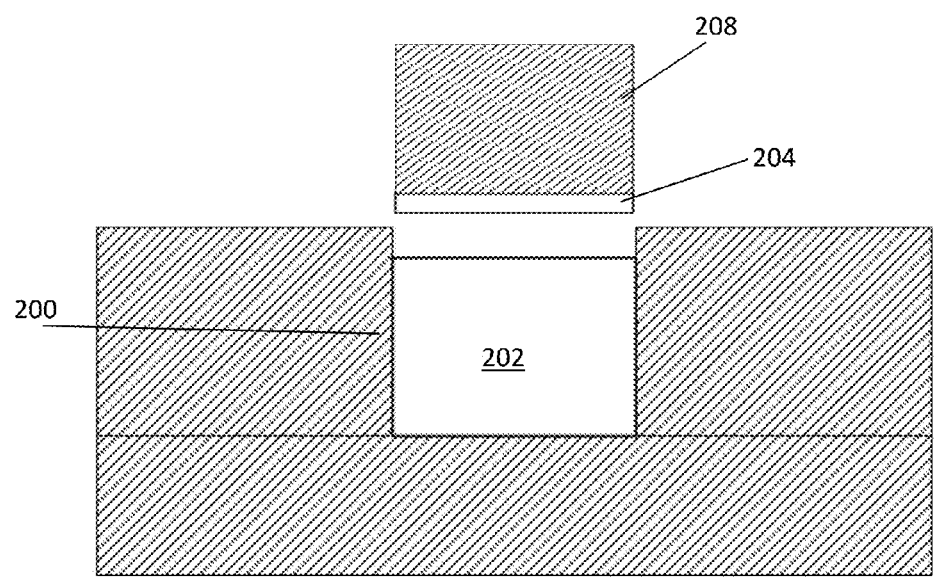
FIG. 4 is another schematic illustration of a method of making an interconnect according an embodiment.

Alternatively, as shown in FIG. 4, the coating powder 204 may be electrostatically attracted to the upper punch 208 of the press. Then, the upper punch 208 presses the coating powder 204 and the lubricant/interconnect powder materials 202 in the mold cavity 200 to form an IC with the coating material 204 embedded in the top of the air side.

Using the above methods, the coating powder may be uniformly incorporated in the surface of the air side of the IC after the compaction step. The compaction step is then followed by sintering and coating steps, such as an MCO and/or LSM coating step by APS or another method described herein.

The ratio of the coating powder and Fe in the Cr—Fe alloy is preferably selected so that the top coating material has a similar coefficient of thermal expansion (CTE) to that of the sintered and oxidized interconnect. The coefficient of thermal expansion of the Cr—Fe alloy is a function of the composition of the alloy and can be chosen by selecting a Cr to Fe ratio. The sintering process may be adjusted to keep the powder oxidized and stable. For example, sintering may be performed using wet hydrogen, or in an inert atmosphere, such as nitrogen, argon or another noble gas. The wet hydrogen or inert gas atmosphere is oxidizing or neutral, respectively, and thereby prevents the oxide powder from reducing.

Figure 5:
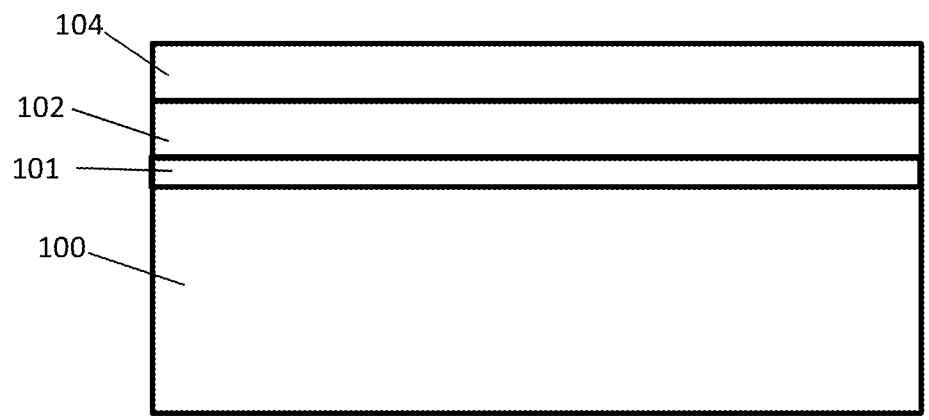
FIG. 5 is a side schematic illustration of an embodiment of an interconnect with a bilayer composite coating.

In fourth embodiment, the coating is a multi-layer composite. FIG. 5 illustrates an example of the fourth embodiment of an IC with a composite coating. The composite coating is composed of a spinel layer 102 and a perovskite layer 104. The spinel layer 102 is deposited first on the Cr alloy (e.g., CrF) interconnect 100. The perovskite layer 104, e.g. the LSM layer described above, is then deposited on top of the spinel layer 102. The native chromium containing interfacial spinel layer 101 may form between the interconnect 100 and layer 102 during layer 102 deposition and/or during high temperature operation of the fuel cell stack containing the interconnect.

Preferably, the lower spinel layer 102 comprises the above described MCO spinel containing Cu and/or Ni. Layer 102 acts as a doping layer that increases the conductivity of the underlying manganese chromium oxide $(Mn, Cr)_3O_4$ or manganese cobalt chromium oxide $(Mn, Co, Cr)_3O_4$ interfacial spinel layer 101. In other words, the Cu and/or Ni from the spinel layer 102 diffuses into the interfacial spinel layer 101 during and/or after formation of layer 101. This results in a Cu and/or Ni doped layer 101 (e.g., $(Mn$ and $Cr)_{3-x-y} Co_x(Cu$ and/or $Ni)_yO_4$ where $(0 \le x \le 1)$, $(0 \le y \le 0.3))$ which lowers layer 101 resistivity.

Layer 102 may comprise the above described Cu containing MCO layer and/or a Ni containing MCO layer and/or a Ni and Cu containing MCO layer. In the MCO layer, when the A element is Mn, the B element is Co, and the spinel is doped with Cu and/or Ni, the spinel family may be described with the general formula $(Mn, Co)_{3-y}(Cu, Ni)_yO_4$, where $(0 \le y \le 0.3)$ More specifically, the spinel family may be described with the following formulas depending on location of the Cu and/or Ni alloying elements:

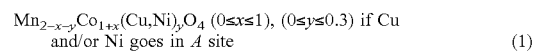
$Mn_{2-x-y}Co_{1+x}(Cu,Ni)_yO_4$ $(0 \le x \le 1)$, $(0 \le y \le 0.3)$ if Cu and/or Ni goes in A site    (1)

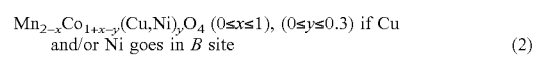
$Mn_{2-x}Co_{1+x-y}(Cu,Ni)_yO_4$ $(0 \le x \le 1)$, $(0 \le y \le 0.3)$ if Cu and/or Ni goes in B site    (2)

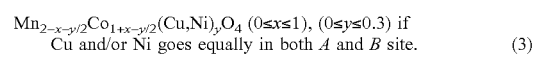
$Mn_{2-x-y/2}Co_{1+x-y/2}(Cu,Ni)_yO_4$ $(0 \le x \le 1)$, $(0 \le y \le 0.3)$ if Cu and/or Ni goes equally in both A and B site.    (3)

While the Cu and/or Ni containing spinel doping layer 102 decreases the ASR of the interconnects, it is permeable to both oxygen and chromium. Thus, in the present embodiment, a second perovskite barrier layer 104 is formed over the doping layer 102. Preferably, layer 104 is a dense LSM layer that reduces or prevents Cr and oxygen diffusion. Layer 104 may be formed with the sintering aid described above to increase its density. The dense layer 104 reduces or prevents the growth of the interfacial spinel layer 101 by blocking diffusion of air and oxygen from the fuel cell cathode side to the CrF IC surface during stack operation. Layer 104 also reduces or prevents chromium poisoning of the fuel cell cathodes in the stack by reducing or preventing chromium diffusion from the ICs to the cathodes.

Thus, the composite coating 102/104 reduces or eliminates the area specific resistance (ASR) degradation contribution from interconnects to the stacks and lowers the overall degradation of the fuel cell stack by reducing or eliminating Cr poisoning of the fuel cell cathodes. First, the spinel doping layer 102 dopes the chromium containing interfacial spinel layer 101 with elements (e.g. Ni and/or Cu) that decrease the resistance of the spinel layer 101. Second, the spinel layer 102 prevents direct interaction between the perovskite 104 layer and the Cr containing interfacial spinel layer 101 which can lead to the formation of unwanted and resistive secondary phases. Third, the spinel (e.g. Mn containing spinel having Co, Cu and/or Ni) layer 102 is less prone to cracking than the LSM layer 104, which enhances the integrity of the coating. Fourth, the top perovskite layer 104 is a second barrier layer that decreases the transport of oxygen to the interfacial oxide 101 on the interconnect surface. The top perovskite layer 104 thus reduces the growth rate of the native oxide layer 101, and decreases transport of chromium from layer 101 to the fuel cell cathodes through the doping layer 102.

Figure 6A:
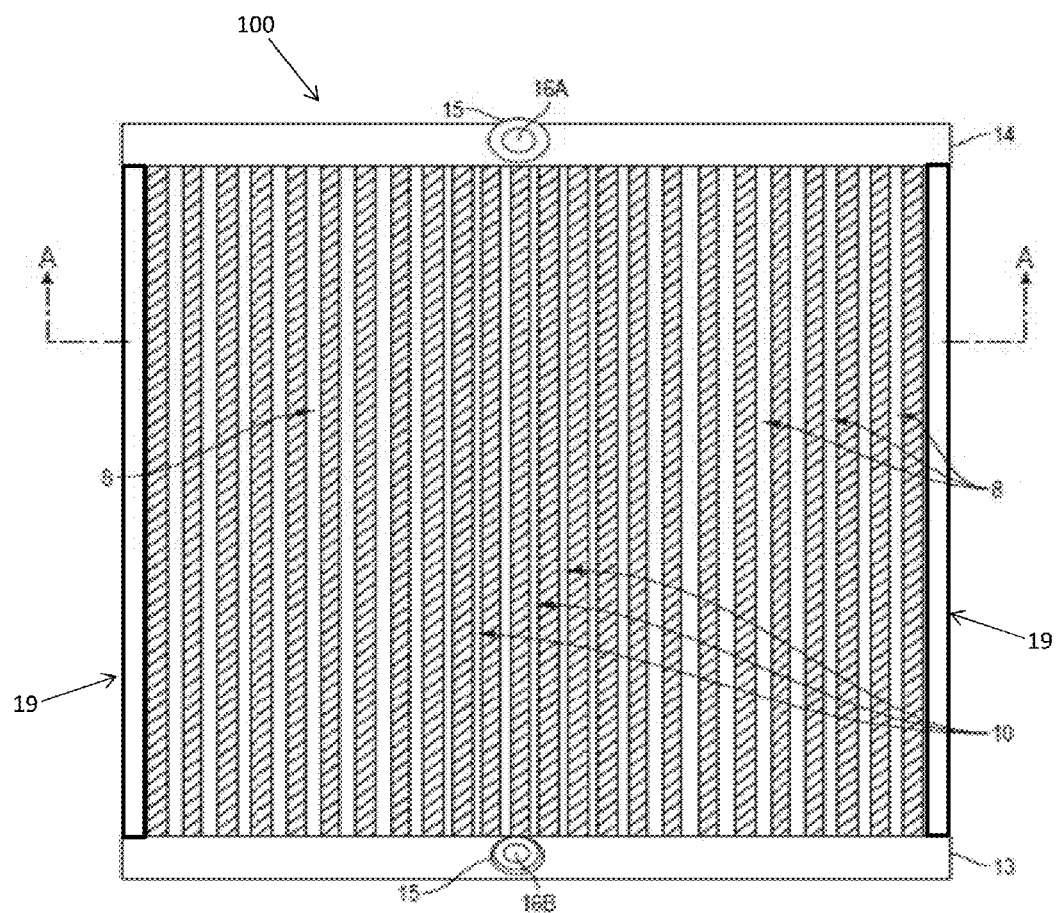
FIGS. 6A-6B and 7 are schematic illustrations illustrating: (6A) the air side of an interconnect according to an embodiment, (6B) a close up view of the seal portion of the air side of the interconnect, (7) the fuel side of the interconnect.

FIG. 6A shows the air side of an exemplary interconnect 100. The interconnect may be used in a stack which is internally manifolded for fuel and externally manifolded for air. The interconnect contains air flow passages or channels 8 between ribs 10 to allow air to flow from one side 13 to the opposite side 14 of the interconnect. Ring (e.g. toroidal) seals 15 are located around fuel inlet and outlet openings 16A, 16B (i.e., through holes 16A, 16B in interconnect 100). Strip seals 19 are located on lateral sides of the interconnect 100.

Figure 6B:
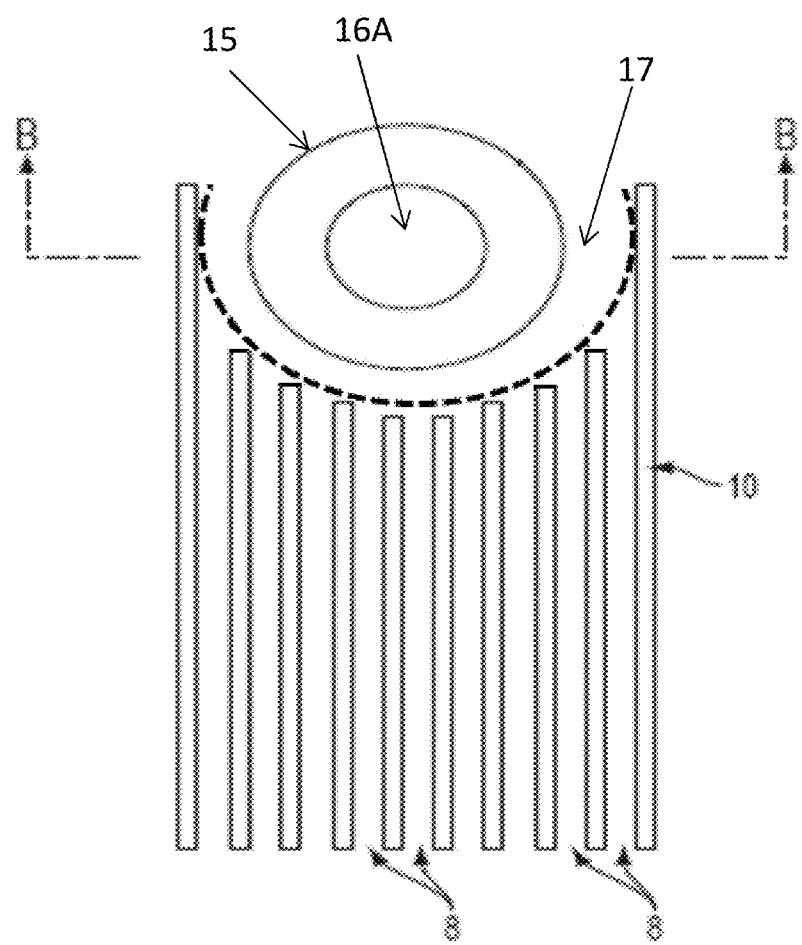

FIG. 6B shows a close up view of an exemplary seal 15, passages 8 and ribs 10. The seals 15 may comprise any suitable seal glass or glass ceramic material, such as borosilicate glass. Alternatively, the seals 15 may comprise a glass ceramic material described in U.S. application Ser. No. 12/292,078 filed on Nov. 12, 2008, incorporated herein by reference.

The interconnect 100 may contain an upraised or boss region below the seal 15 if desired. Additionally, as illustrated in FIG. 6B, the seal 15 is preferably located in a flat region 17 of the interconnect 100. That is, the seal 15 is located in a portion of the interconnect that does not include ribs 10. If desired, the interconnect 100 may be configured for a stack which is internally manifolded for both air and fuel. In this case, the interconnect 100 and the corresponding fuel cell electrolyte would also contain additional air inlet and outlet openings (not shown).

Figure 7:
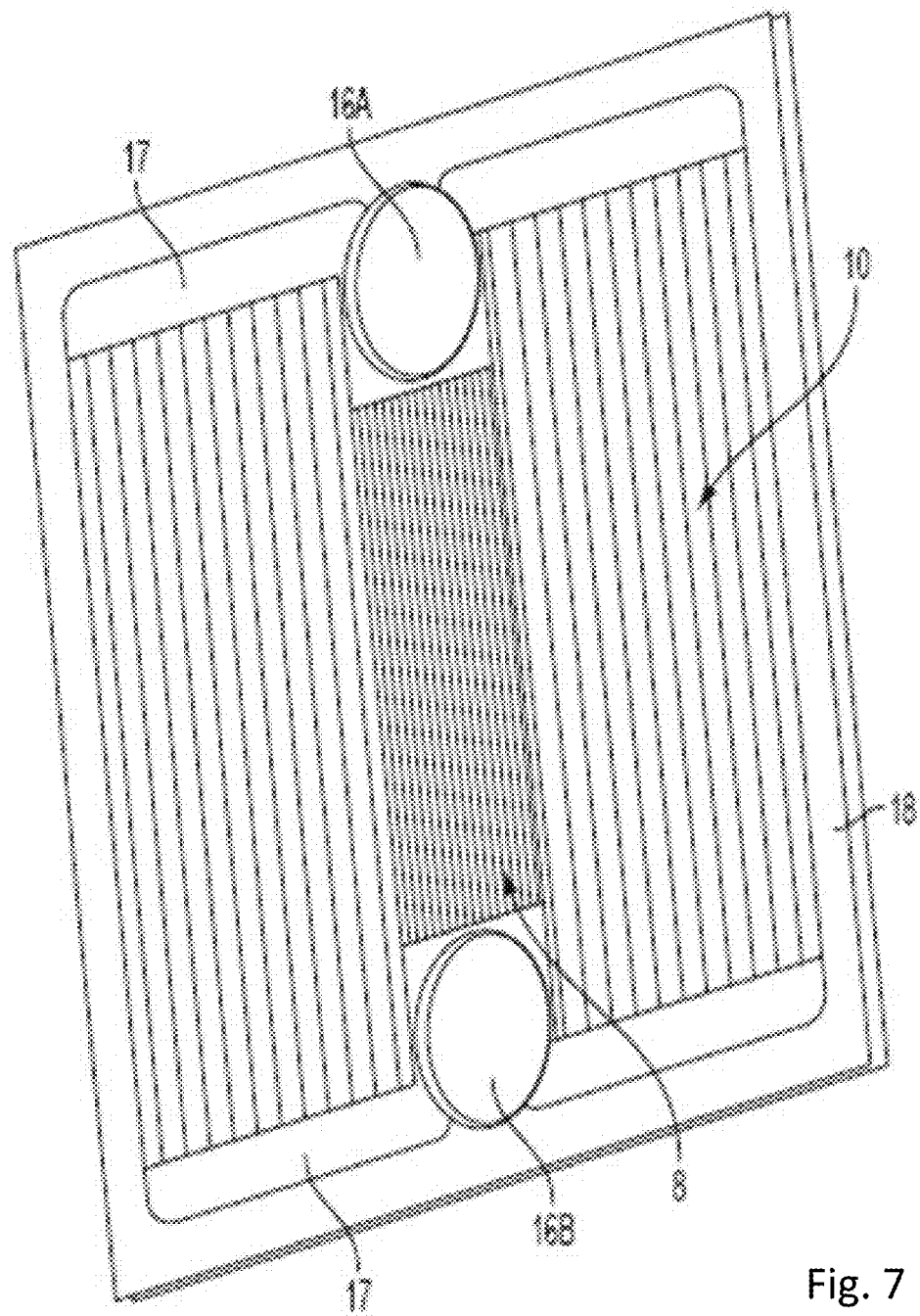

FIG. 7 illustrates the fuel side of the interconnect 100. A window seal 18 is located on the periphery of the interconnect 100. Also shown are fuel distribution plenums 17 and fuel flow passages 8 between ribs 10. It is important to note that the interconnect 100 shown in FIG. 7 has two types of fuel flow passages; however, this is not a limitation of the present invention. The fuel side of an interconnect 100 may have fuel flow passages that are all the same depth and length, or a combination of short and long, and/or deep and shallow passages.

In an embodiment, the interconnect 100 is coated with the $Mn_{1.5}Co_{1.5}O_4$ (MCO) spinel at room temperature using an aerosol spray coating method and further processed with one or more heat treatments. Generally, the MCO coating is omitted in the seal regions (toroid 15, strip 19) by masking or removing MCO deposited in these regions.

The MCO coating may be reduced by the fuel in the riser hole and then reacts with the glass sealing materials at the toroid-shaped seal 15. Thus, in an embodiment, for the interconnect 100 shown in FIG. 6B, the MCO coating is removed from the flat region 17 (e.g., by grit blasting) on the air side of the interconnect before stack assembly and testing. Alternatively, the flat region 17 may be masked during aerosol deposition to prevent coating of the flat region 17. Thus, the MCO coating is omitted in the region 17 under the toroidal seal 15 adjacent to the fuel inlet and/r outlet openings 16A, 16B.

In another embodiment, the interconnect 100 is manufactured by a powder metallurgy process. The powder metallurgy process may result in parts that have connected porosity within the bulk of the interconnect 100 that allows fuel to diffuse from the fuel side to the air side. This fuel transported via the pores may react with the MCO coating on the air side at the coating/interconnect interface. This reaction may lead to seal failure and stack separation. In an embodiment, this failure may be mitigated by omitting the MCO coating under the strip seal 19 by masking the seal 19 locations on the edges of the interconnect during MCO deposition, thereby eliminating coating in these seal areas and allowing the glass seals 19 to bond directly to the metallic interconnect.

Figure 8:
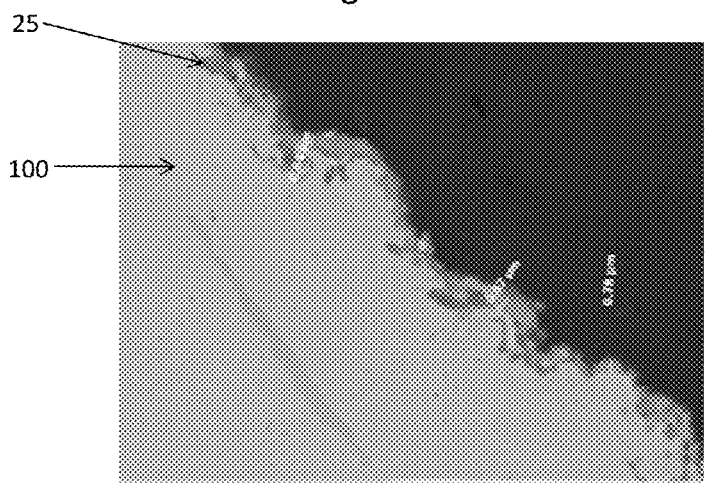
FIG. 8 is a micrograph illustrating chromium oxide on a fuel side (uncoated side) of interconnect after a reduction sintering step.

In another embodiment, interconnects 100 form a thin, green colored $Cr_2O_3$ oxide layer 25 on the fuel side of the interconnect 100. A cross-sectional micrograph of this fuel side oxide is illustrated in FIG. 8. The $Cr_2O_3$ oxide thickness was found to be between 0.5 to 2 microns. Three methods described below may be used to convert or remove this undesirable chromium oxide layer.

In a first embodiment of the method, this oxide layer is removed by any suitable method, such as grit blasting. This method is effective. However, this method is time consuming and adds processing costs.

Alternatively, the $Cr_2O_3$ oxide layer 25 may be left in place and converted to a composite layer. In this embodiment, a nickel mesh anode contact is deposited on the $Cr_2O_3$ oxide layer 25 and allowed to diffuse into the chromium oxide layer. The nickel reacts with the $Cr_2O_3$ oxide layer 25 and forms a Ni-metal/$Cr_2O_3$ composite layer that reduces ohmic resistance of layer 25. If desired, the mesh may be heated after contacting layer 25 to expedite the composite formation.

In another embodiment, oxide layer 25 is reduced or completely eliminated by firing the MCO coated interconnect in an ambient having a low oxygen partial pressure. For instance, based on thermodynamics, $Cr_2O_3$ can be reduced to Cr metal at a $pO_2$ (partial pressure) of $10^{-24}$ atm at 900° C., while CoO reduces to Co-metal at a $pO_2$ of $10^{-16}$ atm at 900° C. By lowering the partial pressure of oxygen (i.e., lowering the dew point) of the firing atmosphere to less than $10^{-24}$ atm at 900° C., the formation of the $Cr_2O_3$ oxide on the fuel side (uncoated side) may be prevented, while allowing the reduction of the MCO coating on the air side of the interconnect to MnO (or Mn metal if $pO_2<10^{-27}$ atm) and Co-metal for sintering benefits. At $pO_2<10^{-27}$ atm, MCO would be reduced to both Mn-metal and Co-metal which may lead to better sintering and denser coatings as compared with MnO/Co-metal. In general, the MCO coated interconnect may be annealed at T>850° C., such as 900° C. to 1200° C., at $pO_2$ of $10^{-24}$ atm, e.g. $10^{-25}$ atm to $10^{-30}$ atm, including $10^{-27}$ atm to $10^{-30}$ atm for 30 minutes to 40 hours, such as 2-10 hours.

In another embodiment described below, formation of the $Cr_2O_3$ oxide layer 25 is reduced or avoided in locations between the nickel mesh anode contact compliant layer and the fuel side of the interconnect.

As described above, in SOFC stacks, a compliant layer, in the form of a nickel is typically introduced, conforming to topographical variation to improve contact with the cell anode electrode. At the beginning of life, simple contact is sufficient to provide the expected power from the active area. However, when interconnects are made predominantly from chromium, then the oxide layer 25 may form on the fuel side during operation due to the water content in the fuel. In the following embodiments, growth of this oxide layer 25 may be reduced or eliminated underneath the Ni mesh.

The present inventors observed that interconnects containing oxide layer 25 growth between the IC and the Ni mesh typically have high voltage losses and degradation rates which are closely related (via ohm's law and active area) to Area Specific Resistance Degradation ("ASRD") rate. Growth of low-conductivity oxides can often contribute to increased ASRD. Conversely, interconnects that feature very little oxide layer 25 growth between the IC and Ni mesh typically have low ASRD. Accompanying this absence of oxide layer 25, the present inventors also observed that the interconnect immediately below the Ni mesh forms a Cr—Fe—Ni alloy. Without wishing to be bound by a particular theory, the present inventors believe that the formation of this Cr—Fe—Ni alloy or a Cr—Ni alloy may lead to achieving a lower ASRD and that this alloy is more resistant to oxide growth than the Cr—Fe interconnect. Thus, it is advantageous to form this alloy under as many points of contact as possible between the Ni mesh and the IC, especially in regions of high current density, such as in the middle portion of the interconnect. Otherwise, during stack operation, current must either force through a layer of resistive oxide 25 that grows later in stack life, or consolidate to higher conductivity points, thereby reducing the effective active area.

Furthermore, the present inventors also believe that the formation of this alloy is influenced by several factors, including compression pressure between the Ni mesh and the interconnect, percent undiffused Fe in the interconnect locally under the Ni mesh, surface contamination between the interconnect and the Ni mesh, attachment of the mesh to the interconnect and/or the addition of nickel to the interconnect alloy. For example, if percent undiffused Fe is low, and contaminants are high, high pressure may be placed to overcome these impediments. In contrast, if the percent of undiffused Fe is increased and/or the contaminant levels are decreased, then less pressure may be placed to avoid ASRD increase.

In the first aspect of the present embodiment, a compression pressure between the Ni mesh and the interconnect in the fuel cell stack is increased to decrease the formation of the chromium oxide layer 25. One way to increase the pressure on the mesh in the stack is to make the interconnect thickness non-uniform to generate a pressure field or gradient on the mesh. Preferably, the interconnect ribs in the middle of the interconnect have a slightly greater height than the ribs in the periphery of the interconnect (i.e., the middle of the interconnect has a slightly greater thickness than the peripheral portions of the interconnect). This creates a pressure field in the middle of the interconnect (where most of the current is produced in the adjacent fuel cells in the stack) and exerts a higher pressure on the nickel mesh contacting the middle of the interconnect than the periphery of the interconnect after the mesh and the interconnect are placed into the fuel cell stack. In turn, this is believed to increase the formation of the Cr—Fe—Ni alloy under the mesh and/or to decrease the ASRD.

In a second aspect of this embodiment, the contamination between the fuel side of the interconnect and the mesh is reduced. This may be accomplished by reducing contaminant presence during the stack manufacture process and/or by cleaning the surface of the interconnect.

In a third aspect of this embodiment, a sufficiently high percent of undiffused iron is maintained at least on the fuel side of the interconnect to form the Cr—Fe—Ni alloy. Undiffused iron includes iron regions that have not been alloyed with the chromium matrix of the interconnect (e.g., in an interconnect having 4-6 wt % Fe and balance Cr with optional 0-1 wt % yttria or yttrium). Achieving a high percent undiffused iron can be achieved through any suitable methods, such as sintering the pressed powder interconnect less and/or starting with larger iron particles. Sintering less includes partially sintering the interconnect at a lower temperature or a shorter duration than that required for fully alloying the pressed iron and chromium powder particles after pressing a chromium and iron containing powder into the interconnect. Larger iron particles are effective at achieving the desired percent undiffused iron for ASRD reduction purposes, but may require longer sintering times and/or higher sintering temperatures. Thus, one method of achieving undiffused iron involves pressing mixture of a chromium powder having a first average particle size and iron powder having a second particle size larger than the first particle size (e.g., 30-200% larger in diameter, such as 50-100% larger) to form the interconnect followed by sintering the interconnect.

In a fourth aspect of this embodiment, the nickel mesh is physically attached to the fuel side surface of the interconnect to prevent the chromium oxide from forming between the mesh and interconnect surface. For example, the nickel mesh may be thermally fused, welded or brazed to the interconnect surface throughout the entire surface of the mesh at least in the middle of the interconnect, and preferably in the middle and periphery of the interconnect. By welding the mesh to the interconnect in plural locations, in particular in the middle of the interconnect where low pressure is often found, the effective active area is increased and high conductivity is found in that active area. Alternatively, the pressed powder Cr—Fe interconnect may placed in contact with the Ni mesh and then sintered while in contact with the Ni mesh below the melting point of Ni (e.g., below 1450 C, such as at 1350-1425 C). This sintering temperature accompanied with an increase in sintering time could maintain the CTE of the part while thermally fusing the Ni mesh to the interconnect in all contact points.

In a fifth aspect of this embodiment, nickel is added to the Cr—Fe interconnect alloy to promote the formation of the Cr—Fe—Ni alloy at least on the fuel surface of the interconnect. Iron powder is added to the base Cr powder to increase the CTE of the interconnect above that of chromium and match the CTE of the solid oxide fuel cell. With Ni having approximately the same CTE as Fe, it is reasonable that Ni can be substituted for Fe. The inclusion of Ni powder into the chromium powder, or chromium and iron (or chromium-iron alloy) powder mix in the powder metallurgy press/mold followed by pressing the powder results in a pressed interconnect part containing the Cr—Ni or Cr—Fe—Ni alloy throughout the part. Furthermore, the compressibility of Co and Ni are slightly higher than Fe, so substituting these elements for Fe would only aid the compaction process. It is known that adding Fe into the Cr matrix reduces the level of oxidation, so keeping some level of Fe may still be advantageous. Thus, all or part of the iron in the interconnect may be substituted by nickel (e.g., 1-100%, such as 10-90%, for example 30-70% of iron in the Cr—Fe (4-6 wt %) alloy may be substituted by nickel to form a Cr-M (4-6 wt %) alloy, where M=1-100% Ni and 99-1 Fe %.

A powder composition adjustment is described in the above embodiments for aiding the function of the coating on the air side of the interconnect by partially substituting LSM, MCO, Co and/or Mn for the Fe in the powder mixture in order to promote the formation of a Mn—Co—Cr spinel layer on the cathode side (air side) of the interconnect.

In another aspect of this embodiment, the alloying elements useful for the air side (e.g., Co and/or Mn) and the fuel side (e.g., Ni) are combined in the Cr—Fe interconnect. Thus, the powder composition placed into the press/mold includes Cr, Fe, Ni and at least one of Co and Mn. However, the Co and/or Mn is only desired on the air side, and the Ni is only desired on the fuel side. The inventors have observed that a certain amount of segregation of the Fe and Cr powder occurs in the press/mold, causing smaller Cr particles to sift downward in the press compaction cavity (i.e., in the mold cavity), causing the fuel side to have a more diluted Fe content, and the air side to have a more concentrated Fe content. This phenomenon can be leveraged to layer the IC with the desired materials by mixing a powder composition and placing it into the compaction cavity where the Ni particle sizes are smaller than the Cr &Fe particles and the Cr & Fe particles are the same size. If the Co and/or Mn containing particles (e.g., Co and/or Mn metal particles and/or the MCO and/or LSM oxide metal particles) are also used, then they are larger than the Cr & Fe particles for interconnects pressed with the air side up. Then, upon filling the compaction cavity, the punch and die can be vibrated to help the segregation process occur. This will cause the Ni to settle on the bottom of the cavity where the fuel side of the interconnect will be formed, the Co and/or Mn to settle on top of the cavity where the air side of the interconnect will be formed and the Fe and Cr to remain in the middle. For interconnects that are pressed with the fuel side up, the Ni particle sizes are larger than the Cr & Fe particles, the Cr & Fe particles are the same size, and the Co and/or Mn containing particles are smaller than the Cr &Fe particles. As used herein, the particle sizes refer to average particle sizes, and the larger particles may have an average particle size that is 25-200% larger than the Fe and Cr average particle size, and the smaller particles may have an average particle size that is 25-200% smaller than the Fe and Cr average particle size The following are non-limiting embodiments of average particle sizes for this embodiment.

If Fe is not needed for chromium oxide management:
2.5% Co, particle size~100 μm
95% Cr, particle size~50 μm
2.5% Ni, particle size~25 μm If Fe is needed for chromium oxide management:
2% Co, particle size~100 μm
95% Cr, particle size~50 μm
1% Fe, particle size~50 μm
2% Ni, particle size~25 μm If a Mn based spinel is formed:
1% Co, Particle size~100 μm
1% Mn, Particle size~100 μm
95% Cr, particle size~50 μm
1% Fe, particle size~50 μm
2% Ni, Particle size~25 μm In another aspect of this embodiment, the nickel powder may be added only to the fuel side of the IC using the method described above with respect to FIGS. 3 and 4. If desired, the nickel powder may be added to the fuel side while Co, Mn, cobalt oxide and/or manganese oxide powder may be added only to the air side of the interconnect.

A method for embedding the alloying material in the top surface of the interconnect is illustrated in FIGS. 3A-3C. The lubricant and Cr/Fe powder 202 which is used to form the bulk of the IC are added to the mold cavity 200 with a first shoe (not shown) or by another suitable method, as shown in FIG. 3A. The alloying material powder 204 (e.g., Ni) or a mix of the alloying material power 204 and lubricant/Cr/Fe powder 202 is provided into the mold cavity using a second shoe 206 over the powder 202 located in the mold cavity before the compaction step, as shown in FIG. 3B. The powders 204, 202 are then compacted using a punch 208, as shown in FIG. 3C, to form the interconnect having the alloying material (e.g., Ni) embedded in its surface on the fuel side (i.e., if the fuel side of the IC is formed facing up in the mold). The air side coating material powder (e.g., LSM, MCO, Co and/or Mn) can be formed on the opposite, bottom side of the interconnect, as described with respect to FIGS. 3A-3C above, before the alloying (e.g., Ni) material is formed on the top side of the interconnect.

Alternatively, the alloying material powder 204 (or a mix of the alloying material power 204 and lubricant/Cr/Fe powder 202) is provided into the mold cavity 200 first. The lubricant/Cr/Fe powder 202 is then provided into the mold cavity 200 over powder 204 before the compaction step if the fuel side of the IC is formed in the mold facing down. In this manner, the Ni is incorporated into the IC primarily at the top of the fuel side surface of the IC. The air side coating material powder (e.g., LSM, MCO, Co and/or Mn) can then be formed on the opposite, top side of the interconnect as described with respect to FIGS. 3A-3C above.

Alternatively, as shown in FIG. 4, the alloying powder 204 (e.g., Ni) may be electrostatically attracted to the upper punch 208 of the press. Then, the upper punch 208 presses the alloying powder 204 and the lubricant/interconnect powder materials 202 in the mold cavity 200 to form an interconnect with the alloying material 204 embedded in the top of the fuel side.

Using the above methods, the alloying powder may be uniformly incorporated in the surface of the fuel side of the interconnect after the compaction step. The compaction step is then followed by sintering and nickel mesh formation steps.

In summary, the formation of a chromium oxide layer is reduced or avoided by at least one of increasing compression pressure between the nickel mesh and the interconnect, providing undiffused Fe in the interconnect under the nickel mesh, reducing surface contamination between the interconnect and the nickel mesh, attaching the nickel mesh to the interconnect, or adding nickel to the interconnect alloy, including combination of any two, three, four or all five of the above steps.

In another embodiment, to reduce costs of the MCO coating process, the MCO coating may be annealed (e.g. fired or sintered) during the sintering step for the powder metallurgy (PM) formed interconnect. The sintering of the powder metallurgy interconnect 100 and of the MCO coating on the interconnect may be conducted in the same step in a reducing ambient, such as a hydrogen reduction furnace with a dew point between −20 and −30° C., at temperatures between 1300 and 1400° C., and for a duration between 0.5 and 6 hrs. At these temperatures and partial pressures of oxygen, the MCO coating will reduce completely to Co-metal and Mn-metal. However, the melting temperature of Mn is around 1245° C., the melting temperature of Co is around 1495° C., and the Co—Mn system has a depressed liquidus line. Thus, sintering at temperatures between 1300 and 1400° C. may result in the formation of an undesirable liquid phase.

Possible solutions to avoid the formation of liquid include lowering the sintering temperature below 1300° C., such as below 1245° C., for example from 1100° C. to 1245° C., increasing the partial pressure of oxygen to reduce the Mn (but not oxidize the Cr) in MCO to MnO (melting temp 1650° C.) as opposed to Mn-metal, decreasing the Mn:Co ratio in MCO to increase the melting temperature of the Mn—Co metal system, adding dopants to MCO, such as Cr, to increase melting temperature of Co—Mn—Cr metal system, and/or adding dopants, such as Fe, V and or Ti to the MCO coating to stabilize binary and ternary oxides (to prevent reduction to metal phase). For example, at a sintering temperature of 1400° C., MnO reduces to Mn-metal at a $pO_2$ of $10^{-17}$ atm while $Cr_2O_3$ reduces to Cr-metal at a $pO_2$ of $10^{-15}$ atm, which gives a small window (a $pO_2$ between $10^{-17}$ and $10^{-15}$ atm) where Cr is reduced to metal yet the MnO stays as an oxide which has a high melting point. Thus, the interconnect and the MCO coating may be sintered at 1300-1400° C. at $pO_2=10^{-15}$–$10^{-17}$ atm.

In another embodiment, the IC sintering step could be conducted first after which the MCO coating is applied to the sintered IC. The IC and coating are then put through a reduction step described in the previous embodiment that is more suitable for the MCO coating.

In another embodiment, interconnect fabrication costs may be reduced by depositing the MCO layer as a mixture of already reduced components such as MnO, CoO, Mn metal, Co metal, or any combination of these constituents. The mixture is then to be sintered, preferably under low $pO_2$ conditions. However, such sintering may be easier or the starting material may be denser, thereby reducing the time for sintering. Additionally, these precursor particles may be much less expensive than MCO precursor, which requires expensive synthesis methods to produce.

Additionally, a grit blast step may be performed before coating the interconnect with the MCO layer to remove the native chromium oxide layer from both the air and fuel sides of the interconnect. To reduce costs, the native oxide may be removed only from the air side of the interconnect before forming the MCO coating on the air side of the interconnect. The MCO coating is then deposited on the air side and the interconnect is anneals as described above. Removal of oxide from the fuel side, such as by grit blasting, may then take place after the anneal is complete. In this manner, the number of grit blast steps is reduced because no additional grit-blast steps are required to remove the oxide growth that occurs on the fuel side of the interconnect during the anneal of the MCO coating.

In other embodiments, the composition of MCO coating is modified to increase stability at SOFC operational temperatures, such as 800-1000° C. The MCO composition of some of the prior embodiments is $Mn_{1.5}Co_{1.5}O_4$. This material has a high electric conductivity. However, the MCO material is reducible to the binary oxides, MnO and CoO, or to the binary oxide MnO and Co-metal.

Figure 9:
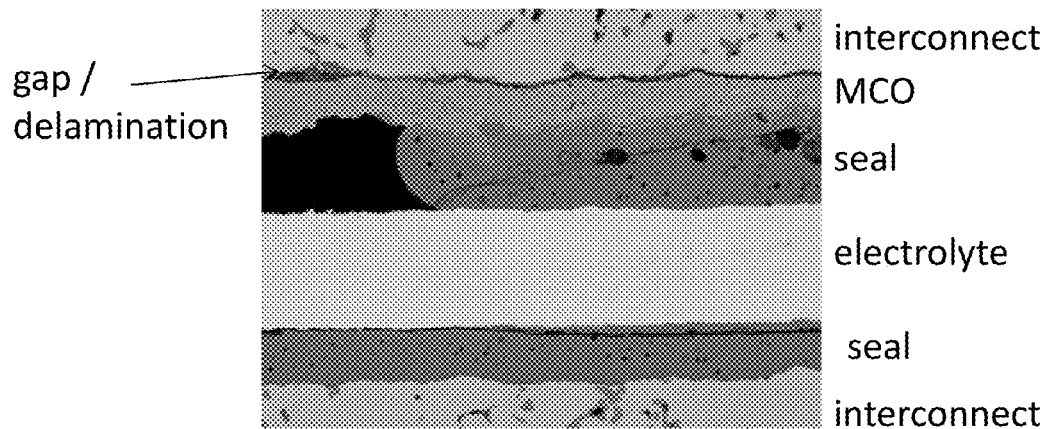
FIG. 9 is a micrograph of a portion of a SOFC stack illustrating reduction of an MCO coating (in a strip seal area) at the coating/IC interface due to fuel diffusing through porous IC.

In some fuel cell geometries, the MCO coating is only directly exposed to the fuel stream at the riser opening(s) 16A, 16B. This fuel/coating interface can be eliminated by not coating the flat region 17 around the opening (FIG. 6B). However, interconnects which are fabricated by a powder metallurgy method results in a part with some connected (open) porosity that can allow fuel to diffuse through the part to the air side. The fuel that diffuses through the pores may react with and reduce the MCO at the MCO/interconnect interface (shown in FIG. 9) resulting in a porous layer consisting of MnO and Co-metal. The coating/IC interface may be compromised, leading to adhesive failure and separation of the cell from the interconnect during routine handling, as shown in FIG. 9.

It is desirable to have a coating material that is more stable and less likely to be reduced when exposed to a fuel environment. The embodiments described below optimize the composition and/or dope the MCO with other elements in order to stabilize the material in a reducing atmosphere.

Figure 11:
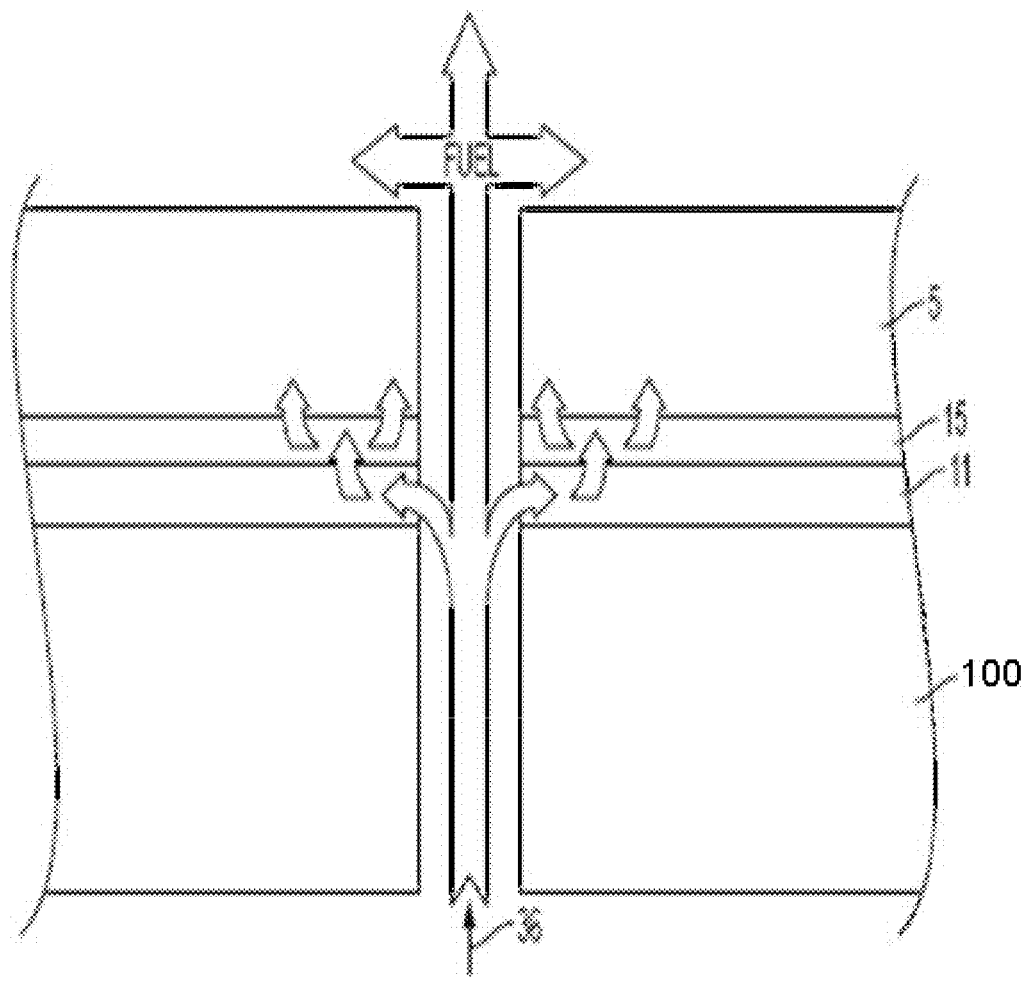
FIG. 11 is a schematic illustration of a fuel inlet riser in a conventional fuel cell stack.
Figure 12:
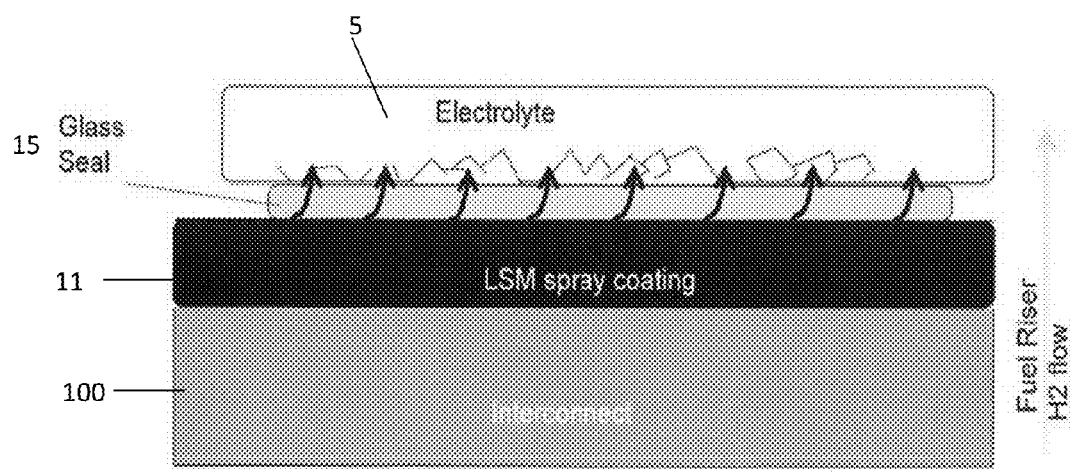
FIG. 12 is a schematic illustration of a SOFC illustrating a theory of electrolyte corrosion.

FIGS. 11 and 12 illustrate a theory of electrolyte corrosion. In the prior art SOFC stack shown in FIGS. 11 and 12, LSM coating 11 on an interconnect is located in contact with the ring seal 15. The seal 15 contacts the cell electrolyte 5. Without wishing to be bound by a particular theory, it is believed that manganese and/or cobalt from the manganese and/or cobalt containing metal oxide (e.g., LSM of LSCo) layer 11 leaches into and/or reacts with the glass seal 15 and is then transported from the glass to the electrolyte. The manganese and/or cobalt may be transported from the glass to the electrolyte as manganese and/or cobalt atoms or ions or as a manganese and/or cobalt containing compound, such as a manganese and/or cobalt rich silicate compound. For example, it is believed that manganese and cobalt react with the glass to form a $(Si, Ba)(Mn,Co)O_{6\pm\delta}$ mobile phase which is transported from the glass seal to the electrolyte. The manganese and/or cobalt (e.g., as part of the mobile phase) at or in the electrolyte 5 tends to collect at the grain boundaries of the zirconia based electrolyte. This results in intergranular corrosion and pits which weaken the electrolyte grain boundaries, ultimately leading to cracks (e.g., opening 16A to opening 16B cracks) in the electrolyte 5. Without being bound by a particular theory, it is also possible that the fuel (e.g., natural gas, hydrogen and/or carbon monoxide) passing through the fuel inlet riser 36 may also react with the metal oxide layer 11 and/or the glass seal 15 to create the mobile phase and to enhance manganese and/or cobalt leaching from layer 11 into the seal 15, as shown in FIG. 11.

As discussed above, in other embodiments, the composition of MCO coating is modified to increase stability at SOFC operational temperatures, such as 800-1000° C. Thus, the MCO composition may be optimized based on stability and electrical conductivity. Example compositions include, but are not limited to, $Mn_2CoO_4$, $Mn_{1.75}Co_{0.25}O_4$, $Co_{1.75}Mn_{0.25}O_4$, $Co_2MnO_4$, and $Co_{2.5}Mn_{0.5}O_4$.

Figure 10:
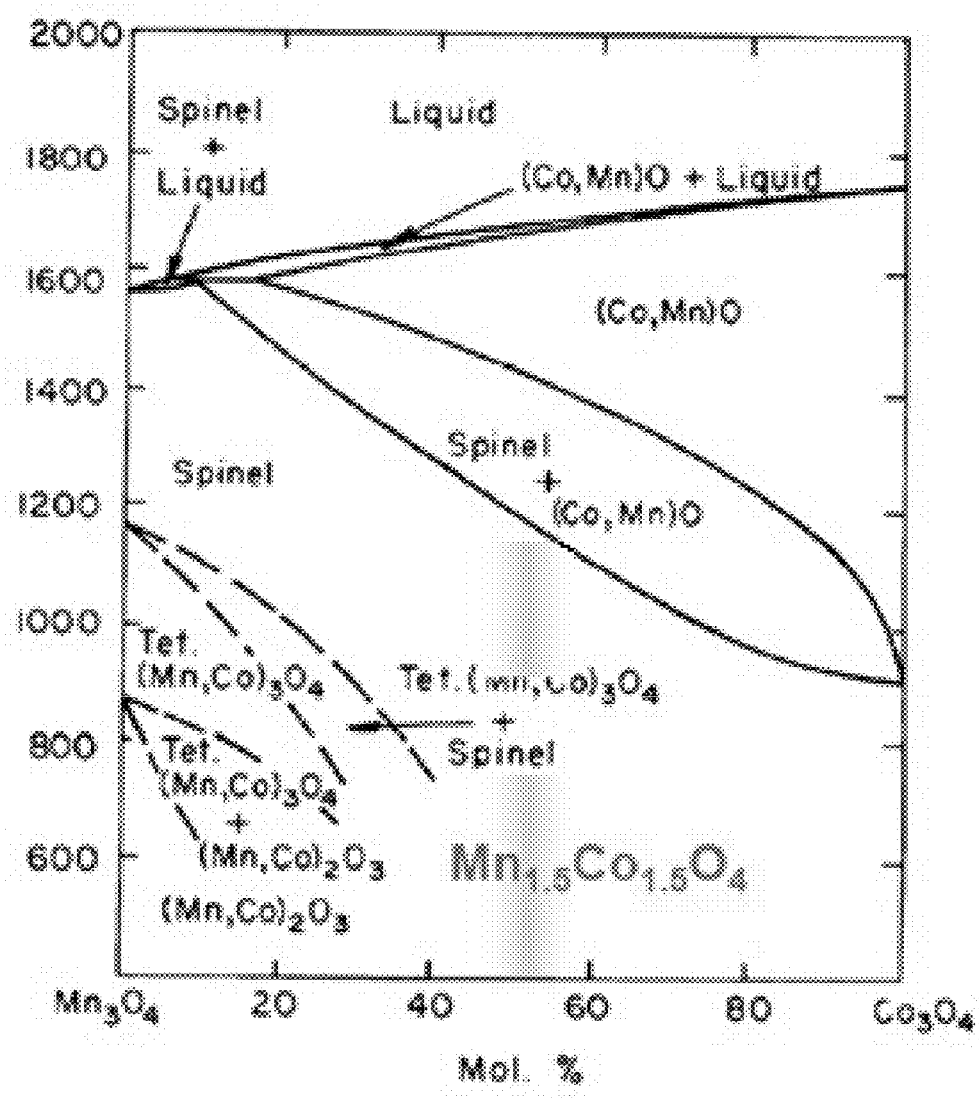
FIG. 10 is a phase diagram illustrating the $Mn_3O_4$—$Co_3O_4$ system.

Based on the phase diagram (FIG. 10) and from a stability point of view, it may be beneficial to have a multi-phased composition rich in Mn such as $Mn_{2.5}Co_{0.5}O_4$ and $Mn_{2.75}Co_{0.25}O_4$ (e.g. Mn:Co atomic ration of 5:1 or greater, such as 5:1 10 11:1. A higher Mn content may also result in a more stable composition because the composition is in a higher oxidation state than the two phase spinel+binary oxide found at high Co content. However, any composition in the $(Mn,Co)_3O_4$ family between the end compositions of $Co_3O_4$ and $Mn_3O_4$ may be suitable.

In another embodiment, MCO is stabilized by adding an additional dopant that is less prone to reduction. For example, it is known that MCO reacts with Cr in the IC alloys to form $(Cr, Co, Mn)_3O_4$ spinel. If Cr is added intentionally to the MCO coating in low levels, such as 0.1 atomic % to 10%, this would result in a spinel $(Cr, Co, Mn)_3O_4$ which is more stable than MCO because $Cr^{3+}$ is very stable. Other transition metal elements that are soluble in the spinel structure which may increase stability include Fe, V, and Ti. Example coating materials include the spinel $(Fe, Co, Mn)_3O_4$ with 1% to 50 at % Fe, $(Ti, Co, Mn)_3O_4$ with 1% to 50% Ti, or a combination of $(Fe, Ti, Co, Mn)_3O_4$.

The addition of Ti may lead to more stable secondary phases including $Co_2TiO_4$, $MnTi_2O_4$, or $FeTi_2O_4$. These phases benefit overall coating stability. Spinels with any combination of the above mentioned dopants are possible including $(Fe, Cr, Co, Mn)_3O_4$, $(Cr, Ti, Co, Mn)_3O_4$, etc.

It is known that spinels based on Mg, Ca, and Al are very stable and resist reduction. However, these spinels have low electrical conductivity and thus are not preferred for application as an interconnect coating. In contrast, low levels of doping of Ca, Mg, and/or Al into a conductive spinel, such as MCO, increases the stability of the material while only marginally lowering the electrical conductivity. Example spinels include $(Ca, Co, Mn)_3O_4$ with 1% to 10 at % Ca, $(Mg, Co, Mn)_3O_4$ with 1% to 10 at % Mg, $(Al, Co, Mn)_3O_4$ with 1% to 10 at % Al, or combinations such as $(Ca, Al, Mn, Co)_3O_4$, where Ca, Al and/or Mg are added at 1-10 at %. Si and Ce are other elements that may be use as dopants (1-10 at %) for the MCO spinel.

In addition to the methods described above that fall in the general category of material-specific stabilization efforts, alternative embodiments are drawn to design changes that can be made that improve the stability of the coating, either in combination with or in the alternative to the above embodiments. In a first alternative embodiment, a stable barrier layer can be added to the interconnect before the addition of the MCO coating. This barrier layer would preferably be made of a more stable oxide than MCO and would be conductive and thin enough to not detrimentally affect the conductivity of the interconnect component. Further, this barrier layer is preferably dense and hermetic. Example barrier layers include, but are not limited to, a doped Ti-oxide (e.g. $TiO_2$) layer or lanthanum strontium manganate (LSM).

A second alternative embodiment includes the addition of a reactive barrier layer between the interconnect and the MCO coating which includes any of the elements discussed above (e.g. Cr, V, Fe, Ti, Al, Mg, Si, Ce and/or Ca) as possible dopants. This layer diffuses these element(s) into the MCO coating upon heating the interconnect to standard operating temperatures (800-1000° C.), creating a graded doping profile with higher concentration of dopant at the interconnect interface where reduction occurs. In this manner, a majority of the coating contains relatively little dopant and hence the conductivity may be less affected than by a uniform doping of the coating material. A reactive layer is a metal layer (e.g. Ti or metal containing compound that allows outdiffusion of the metal at 800° C. or higher.

A third embodiment includes designing the interconnect material to contain a reactive doping element (e.g. Si, Ce, Mg, Ca, Ti and/or Al for a Cr-4-6% Fe interconnect) that diffuses into the MCO coating in the same manner just described. Thus, the interconnect would contain ≥90 wt % Cr, 4-6% Fe and 0.1-2% Mg, Ti, Ca and/or Al.

Additionally, any method of deposition or treatment of the IC to reduce or close the porosity of the part, beyond the standard oxidation methods, would help limit the reduction of the MCO coating. For example, a Cr layer may be electroplated onto the porous part before the MCO annealing step to further reduce the porosity. Or, as described above, the addition of a reactive barrier layer, if dense and hermetic, would also reduce or block hydrogen diffusion from surface pores.

Although the foregoing refers to particular preferred embodiments, it will be understood that the invention is not so limited. It will occur to those of ordinary skill in the art that various modifications may be made to the disclosed embodiments and that such modifications are intended to be within the scope of the invention. All of the publications, patent applications and patents cited herein are incorporated herein by reference in their entirety.

What is claimed is:

1. A method of making an interconnect for a solid oxide fuel cell stack, comprising:
    providing a chromium alloy interconnect; and
    providing a nickel mesh in contact with a fuel side of the interconnect;
    wherein formation of a chromium oxide layer is reduced or avoided in locations between the nickel mesh and the fuel side of the interconnect.

2. The method of claim 1, further comprising a Cr—Ni alloy or a Cr—Fe—Ni alloy located at least in the fuel side of the interconnect under the nickel mesh.

3. The method of claim 1, wherein the formation of the chromium oxide layer is reduced or avoided by at least one of increasing compression pressure between the nickel mesh and the interconnect, providing undiffused Fe in the interconnect under the nickel mesh, reducing surface contamination between the interconnect and the nickel mesh, attaching the nickel mesh to the interconnect, or adding nickel to the interconnect alloy.

4. The method of claim 3, wherein the formation of the chromium oxide layer is reduced or avoided by at least two of increasing compression pressure between the nickel mesh and the interconnect, providing undiffused Fe in the interconnect under the nickel mesh, reducing surface contamination between the interconnect and the nickel mesh, attaching the nickel mesh to the interconnect, and adding nickel to the interconnect alloy.

5. The method of claim 3, wherein the formation of the chromium oxide layer is reduced or avoided by increasing the compression pressure between the nickel mesh and the interconnect by generating a pressure field or gradient on the mesh.

6. The method of claim 5, wherein interconnect ribs in a middle of the interconnect have a greater height than interconnect ribs in a periphery of the interconnect to generate the pressure field or gradient on the mesh in a solid oxide fuel cell stack.

7. The method of claim 3, wherein the formation of the chromium oxide layer is reduced or avoided by providing the undiffused Fe in the interconnect under the nickel mesh.

8. The method of claim 7, wherein providing the undiffused Fe in the interconnect under the nickel mesh comprises pressing a chromium and iron containing powder to form the interconnect followed by partially sintering the interconnect at a lower temperature or a shorter duration than that required for fully alloying the iron and chromium powder particles.

9. The method of claim 7, wherein providing the undiffused Fe in the interconnect under the nickel mesh comprises pressing mixture of a chromium powder having a first average particle size and iron powder having a second particle size larger than the first particle size to form the interconnect followed by sintering the interconnect.

10. The method of claim 3, wherein the formation of the chromium oxide layer is reduced or avoided by attaching the nickel mesh to the interconnect using thermal fusing or welding.

11. The method of claim 3, wherein the formation of the chromium oxide layer is reduced or avoided adding nickel to the interconnect alloy.

12. The method of claim 11, wherein the nickel fully or partially substitutes iron at least in a fuel side of the interconnect.

13. The method of claim 12, wherein the nickel fully or partially substitutes iron only in the fuel side of the interconnect by providing nickel powder having a different average particle size than chromium powder in a mold cavity.

14. The method of claim 12, wherein the nickel fully or partially substitutes iron only in the fuel side of the interconnect by:
   providing first metallic powder particles comprising Cr and Fe in a mold cavity;
   providing second powder particles comprising nickel in the mold cavity; and
   compacting the first and second powder particles to form the interconnect.

15. The method of claim 14, wherein the first powder particles are provided in the mold cavity first and the second powder particles provided on top of the first powder particles in the mold cavity.

16. The method of claim 14, wherein the second powder particles are provided in the mold cavity first and the first powder particles provided on top of the second powder particles in the mold cavity.

17. The method of claim 14, wherein:
   the first or the second powder particles are provided to the mold first and the other ones of the first or the second powder particles are electrostatically attracted to a bottom surface of a punch used to compact the powder particles; and
   the punch presses the first powder and the second powder to compact the first and the second power particles.

18. An interconnect for a solid oxide fuel cell stack, comprising:
   a chromium alloy interconnect; and
   a nickel mesh in contact with a fuel side of the interconnect;
   wherein a Cr—Ni alloy or a Cr—Fe—Ni alloy is located at least in the fuel side of the interconnect under the nickel mesh.

19. The interconnect of claim 18, wherein interconnect ribs in a middle of the interconnect have a greater height than interconnect ribs in a periphery of the interconnect to generate a pressure field or gradient on the mesh in a solid oxide fuel cell stack.

20. The interconnect of claim 18, wherein undiffused Fe is located in the fuel side of the interconnect under the nickel mesh.

21. The interconnect of claim 18, wherein the nickel mesh is welded or thermally fused to the interconnect.

22. The interconnect of claim 18, wherein the interconnect alloy contains nickel.

* * * * *